United States Patent
Komatsu et al.

(10) Patent No.: US 6,875,860 B2
(45) Date of Patent: Apr. 5, 2005

(54) METHOD FOR PURIFYING 5'-PROTECTED THYMIDINES AND NOVEL DERIVATIVES THEREOF

(75) Inventors: Hironori Komatsu, Mobara (JP); Toshiyuki Kouno, Mobara (JP); Katsutoshi Tsuchiya, Mobara (JP); Hiroharu Tanikawa, Mobara (JP); Hiroki Ishibashi, Omuta (JP)

(73) Assignee: Mitsui Chemicals, Inc., Tokyo (JP)

( * ) Notice: Subject to any disclaimer, the term of this patent is extended or adjusted under 35 U.S.C. 154(b) by 120 days.

(21) Appl. No.: 10/144,802

(22) Filed: May 15, 2002

(65) Prior Publication Data

US 2003/0004331 A1 Jan. 2, 2003

(30) Foreign Application Priority Data

May 15, 2001 (JP) ........................................ 2001-144278

(51) Int. Cl.⁷ ........................ C07H 19/073; B01D 9/02
(52) U.S. Cl. .................. 536/28.53; 536/28.54
(58) Field of Search ............................ 536/28.53, 28.54; 544/314

(56) References Cited

FOREIGN PATENT DOCUMENTS

| EP | 90789 A1 | * 10/1983 |
| JP | 58-180500 A | 10/1983 |
| JP | 60-152495 A | 8/1985 |
| JP | 6-507883 A | 9/1994 |
| JP | 11-511480 A | 10/1999 |
| JP | 2000-264897 A | 9/2000 |
| WO | WO 00/39138 A1 | 7/2000 |
| WO | WO 00/75154 A2 | 12/2000 |

OTHER PUBLICATIONS

Desiraju, Gautam R., Nature 412, 397–400 (2001).*
Schaller, H. et al, JACS, vol. 85, 1963, pp. 3821–3827.*
Prahadeeswaran, D.; Kolappan, S.; Krishnan, R.; Seshadri, T. P., Journal of Inclusion Phenomena and Macrocyclic Chemistry 37(1–4), 281–297 (English) 2000.*
Baur, Werner H. Nova Acta Leopoldina (1999), 79(310, "Can Crystal Structures Be Predicted?"), pp. 47–57, Chemical Abstracts, 131:187376.*
Joachim Ulrich, "Kirk–Othmer Encyclopedia of Chemical Technology", John Wiley & Sons, 2002.).*
West, Anthony R., Solid State Chemistry and its Applications, Wiley, New York, 1988, pp. 358 & 365.*
S.A. Narang, et al., "[61] Chemical Synthesis of Deoxyoligonucleotides by the Modified Triester Method", Methods in Enzymology, vol. 65, pp. 610–620, 1980.

* cited by examiner

Primary Examiner—Thomas C. McKenzie
(74) Attorney, Agent, or Firm—Burns, Doane, Swecker & Mathis, LLP

(57) ABSTRACT

This invention provides a method for efficiently purifying 5'-protected thymidines which cannot be efficiently purified by the prior art. Impurities can be separated by obtaining crystals including a carbonyl-containing solvent to provide a highly pure 5'-protected thymidine. Thus, this invention allows 5'-protected thymidines, which cannot be purified in an industrial scale by the prior art, to be easily provided with a high purity in a large scale.

8 Claims, No Drawings

METHOD FOR PURIFYING 5'-PROTECTED THYMIDINES AND NOVEL DERIVATIVES THEREOF

FIELD OF THE INVENTION

The present invention relates to a method for purifying a 5'-protected thymidine and a derivative thereof. This invention also relates to a solvent inclusion compound of a 5'-protected thymidine compound obtained as crystals from the method of the present invention.

DESCRIPTION OF THE RELATED ART

5'-protected thymidines are compounds useful as a raw material for an antisense DNA or the like, which has recently been developed.

In recent years, with developments in manufacturing genomic drugs, antisense DNA drugs or the like have rapidly been developed. Therewith, a DNA oligomer used as a raw material, and further, protected deoxynucleosides used as raw materials for the oligomer are increasingly demanded. Regarding the pharmaceutical uses, it is necessary to use an extremely highly purified intermediate product to reduce generation of by-products formed based on impurities to a minimum.

A 5'-protected thymidine has been conventionally isolated and purified by column chromatography, as described in Japanese Patent Laid-Open Nos. 6-507883 and 2000-264897, and Methods of Enzymol., 65 (1980). By this method, separation of impurities greatly different in their polarities or structures may be carried out relatively easily, but elimination of impurities having a similar structure is difficult. In particular, there are many cases where it is difficult to eliminate a 3'-substituted isomer that is an especially problematic impurity. In addition, since this method needs a large-scale purification device, in view of mass production and mass supply in the future, it cannot help saying that this method has a large problem.

Attempts to eliminate impurities without using column chromatography have been made. As an example of a method using a single solvent, Japanese Patent Laid-Open No. 58-180500 has disclosed a purification method using benzene, but in a practical use, the method gives a gel incorporating impurities rather than crystals and is, therefore, impractical. Furthermore, the method has a disadvantage that benzene, which is toxic, is used as a solvent. Japanese Patent Laid-Open No. 11-511480 and PCT Publication No. WO 200075154 have disclosed purification by reprecipitation. Reprecipitation is a method in which, after a crude compound is dissolved in a soluble solvent, the compound is compulsively reprecipitated by addition of an insoluble solvent or dropping into an insoluble solvent. Consequently, its purification ability is basically low. Moreover, it is industrially difficult to appropriately control the amount ratio between the soluble solvent and the insoluble solvent. In addition, where the amount ratio of these solvents is set inappropriately, it easily results in oilification or generates a viscous precipitate so that purification is apt to end in failure. Actually, as described in Japanese Patent Laid-Open No. 60-152495, in some cases, the purified product is obtained as a viscous syrup, and, from an industrial viewpoint, this is a problem. Although some methods of forming amorphous material by reprecipitation has been disclosed till now, no methods for obtaining a crystal by crystallization or recrystallization are known.

SUMMARY OF THE INVENTION

The present invention has been completed in view of the conventional problems. Thus, an object of the present invention is to provide an efficient process for producing an extremely pure 5'-protected thymidine compound with no special facilities.

As a result of intensive studies by the present inventors directed toward the above object, it has been found that, using a carbonyl compound such as butyl acetate and 4-methyl-2-pentanone, a 5'-protected thymidine compound can be obtained as a solvated complex including the solvent and be purified by a purification method such as crystallization or recrystallization, thereby completing the present invention.

Thus, the present invention includes the following aspects:

(1) a method for purifying a 5'-protected thymidine, comprising the steps of:

obtaining a compound represented by formula [1]:

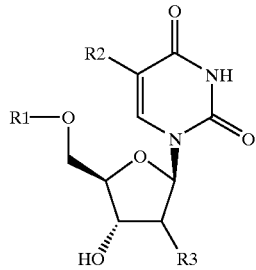

wherein $R^1$ represents optionally substituted trityl; $R^2$ represents hydrogen or lower alkyl; and $R^3$ represents hydrogen, halogen or substituted hydroxyl, in the form of inclusion crystals including a solvent, in a liquid medium comprising the inclusion solvent; and recovering the inclusion crystals from the liquid medium;

(2) the method for purifying a 5'-protected thymidine according to the above section (1), wherein the inclusion solvent is a carbonyl compound represented by formula [2]:

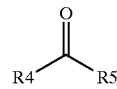

wherein $R^4$ represents lower alkyl; and $R^5$ represents lower alkyl or lower alkoxy;

(3) the purification method according to the above section (2) wherein the carbonyl compound is butyl acetate or 4-methyl-2-pentanone;

(4) the purification method according to any of the above sections (1) to (3), wherein a crude preparation comprising the compound of formula [1] and a compound of formula [3]:

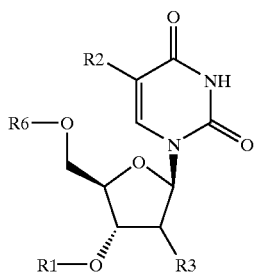

[3]

wherein R⁶ represents hydrogen or optionally substituted trityl; and R¹, R² and R³ are as defined above, is dissolved in the liquid medium and the compound of formula [3] is removed into the liquid medium by recovering the compound of formula [1] in the form of inclusion crystals from the liquid medium;

(5) the purification method according to any of the above sections (1) to (4), wherein the compound of formula [1] is a compound represented by formula [4]:

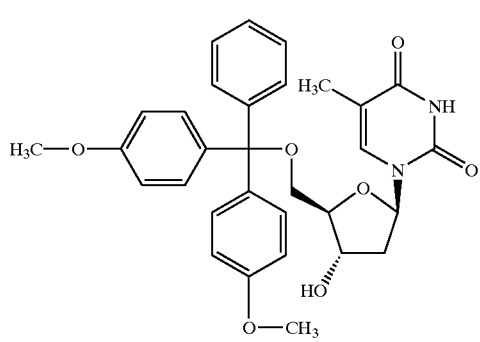

[4]

(6) the purification method according to any of the above sections (1) to (5), wherein the inclusion crystals of the compound of formula [1] including the inclusion solvent are recrystallized from a liquid medium consisting of the inclusion solvent;

(7) the purification method according to any of the above (1) to (6), wherein the liquid medium consists of a single inclusion solvent;

(8) An inclusion compound represented by formula (5):

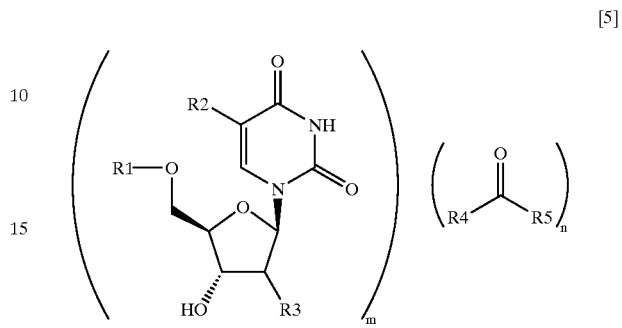

[5]

wherein m and n independently represent an arbitrary integer; R¹, R², R³, R⁴ and R⁵ are as defined above; and (9) An inclusion compound represented by formula (6):

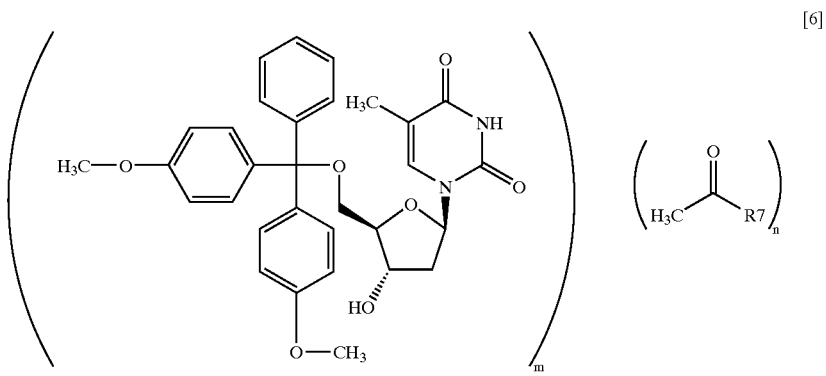

[6]

wherein R⁷ represents n-butoxy or isobutyl; m and n are as defined above.

DETAILED DESCRIPTION OF THE PREFERRED EMBODIMENTS

The present invention will be described in detail below.

R1 in formula [1] is substituted or unsubstituted trityl. A trityl may have a substituent or substituents on at least one of its three phenyl rings. On such a phenyl ring, substitution may be at 2-, 3- or 4-position, or at two or more positions. When one phenyl ring has two or more substituents, the plurality of substituents may be the same or may consist of at least two different types. When two or more phenyl rings are substituted, these substituted phenyl rings may be the same or consist of at least two different types, including a case that two or three phenyl rings have the same substituent or different substituents.

Examples of a substituent on a phenyl in the trityl group include alkyl such as methyl, ethyl and isopropyl; alkyloxy such as methoxy, ethoxy, n-propyloxy and isopropyloxy; nitro; substituted or unsubstituted amino such as amino, methylamino, ethylamino, n-propylamino, isopropylamino, dimethylamino and diethylamino; halogen such as fluoro, chloro, bromo and iodo; acyl such as formyl, acetyl, propionyl and benzoyl; acyloxy such as formyloxy, acetyloxy, propionyloxy and benzoyloxy; and amide such as formamide, acetamide and benzamide. When a plurality of substituents are present, each substituent may be independently selected from the above groups. The alkyl groups in the above various substituents may be preferably lower alkyl groups having 1 to 7 carbon atoms, more preferably ones having the carbon atom numbers in the above concrete examples.

Examples of an optionally substituted trityl include, but not limited to, trityl, 4-methoxytrityl, 4,4'-dimethoxytrityl, 4,4',4"-trimethoxytrityl, 4-methyltrityl and 4,4'-dimethyltrityl.

A lower alkyl group in $R^2$ may be straight or branched. Alternatively, it may form a ring. The alkyl may have an additional substituent. Examples of the lower alkyl group include alkyl groups having 1 to 7 carbon atoms such as methyl, ethyl, n-propyl, isopropyl, butyl, cyclopropyl, cyclopropylmethyl and cyclopentyl.

Halogen in $R^3$ is fluorine, chlorine, bromine or iodine. Substituted hydroxyl in $R^3$ represents hydroxyl substituted with a substituent which can be generally a protective group for hydroxyl such as carboxylate, sulfonate, ether, urethane and silyl. Examples of the groups for protection of the hydroxyl group include unsubstituted or substituted alkyl such as methyl, ethyl, isopropyl, n-butyl, isobutyl, t-butyl, pentyl, benzyl, 2-methoxybenzyl, 3-methoxybenzyl, 4-methoxybenzyl, 2-methylbenzyl, 3-methylbenzyl, 4-methylbenzyl, methoxyethyl, ethoxyethyl, benzyloxymethyl, benzyloxyethyl, acetoxymethyl, acetoxyethyl, benzoyloxymethyl, benzoyloxyethyl, methoxyethoxyethyl, propargyl and allyl; aryl such as phenyl, 2-methoxyphenyl, 3-methoxyphenyl, 4-methoxyphenyl, 4-phenylphenyl, 2-pyridinyl, 3-pyridinyl and 4-pyridinyl; acyl such as formyl, acetyl, propionyl, benzoyl, 2-methoxybenzoyl, 3-methoxybenzoyl, 4-methoxybenzoyl, 2-methylbenzoyl, 3-methylbenzoyl, 4-methylbenzoyl, 2-nitrobenzoyl, 3-nitrobenzoyl, 4-nitrobenzoyl, 4-phenylbenzoyl, 2-chlorobenzoyl, 3-chlorobenzoyl and 4-chlorobenzoyl; urethane such as aminocarbonyl, dimethylaminocarbonyl, methylaminocarbonyl, ethylaminocarbonyl, diethylaminocarbonyl and phenylaminocarbonyl; sulfonate such as methanesulfonyl, ethanesulfonyl, benzenesulfonyl, 2-methylbenzenesulfonyl, 3-methylbenzenesulfonyl, 4-methylbenzenesulfonyl, trifluoromethanesulfonyl and trichloromethanesulfonyl; and silyl such as trimethylsilyl, triethylsilyl, t-butyldimethylsilyl and t-butyldiphenylsilyl.

Examples of substituted hydroxyl in $R^3$ include methoxy, ethoxy, isopropyloxy, n-butyloxy, isobutyloxy, t-butyloxy, pentyloxy, benzyloxy, 2-methoxybenzyloxy, 3-methoxybenzyloxy, 4-methoxybenzyloxy, 2-methylbenzyloxy, 3-methylbenzyloxy, 4-methylbenzyloxy, methoxyethyloxy, ethoxyethyloxy, benzyloxymethoxy, benzyloxyethoxy, acetoxymethoxy, acetoxyethoxy, benzoyloxymethoxy, benzoyloxyethoxy, methoxyethoxy, propargyloxy, allyloxy, phenyloxy, 2-methoxyphenyloxy, 3-methoxyphenyloxy, 4-methoxyphenyloxy, 4-phenylphenyloxy, 2-pyridinyloxy, 3-pyridinyloxy, 4-pyridinyloxy, formyloxy, acetyloxy, propionyloxy, benzoyloxy, 2-methoxybenzoyloxy, 3-methoxybenzoyloxy, 4-methoxybenzoyloxy, 2-methylbenzoyloxy, 3-methylbenzoyloxy, 4-methylbenzoyloxy, 2-nitrobenzoyloxy, 3-nitrobenzoyloxy, 4-nitrobenzoyloxy, 4-phenylbenzoyloxy, 2-chlorobenzoyloxy, 3-chlorobenzoyloxy, 4-chlorobenzoyloxy, aminocarbonyloxy, dimethylaminocarbonyloxy, methylaminocarbonyloxy, ethylaminocarbonyloxy, diethylaminocarbonyloxy, phenylaminocarbonyloxy, methanesulfonyloxy, ethanesulfonyloxy, benzenesulfonyloxy, 2-methylbenzenesulfonyloxy, 3-methylbenzenesulfonyloxy, 4-methylbenzenesulfonyloxy, trifluoromethanesulfonyloxy, trichloromethanesulfonyloxy, trimethylsilyloxy, triethylsilyloxy, t-butyldimethylsilyloxy and t-butyldiphenylsilyloxy.

The alkyl groups in the above various substituents in the protective groups for the hydroxyl group may be preferably lower alkyl groups having 1 to 7 carbon atoms, more preferably ones having the carbon atom numbers in the above concrete examples.

Examples of a lower alkyl group in $R^4$ and $R^5$ in formula [2] include alkyl groups having 1 to 7 carbon atoms such as methyl, ethyl, n-propyl, isopropyl, n-butyl, isobutyl, t-butyl, n-pentyl, 2-methylbutyl, amyl, n-hexyl, cyclopentyl, cyclohexyl and n-heptyl. Examples of the lower alkoxy group in $R^5$ include alkoxy groups having 1 to 6 carbon atoms such as methoxy, ethoxy, isopropyloxy, n-butoxy, isobutyloxy, t-butyloxy and pentyloxy.

An inclusion solvent used in this invention for preparation of the inclusion crystals is preferably a carbonyl compound having carbonyl represented by formula [2]. Examples of such a solvent include acetone, 2-butanone, 3-pentanone, 2,4-dimethyl-3-pentanone, 4-methyl-2-pentanone, 3-methyl-2-butanone, methyl acetate, ethyl acetate, n-propyl acetate, isopropyl acetate, n-butyl acetate, t-butyl acetate, isobutyl acetate, amyl acetate, n-pentyl acetate, n-hexyl acetate, cyclohexyl acetate, n-propyl propionate and isopropyl propionate. These carbonyl compounds are usually used alone in a solvent, but two or more carbonyl compounds may be combined at a mixable ratio. Alternatively, a plurality of carbonyl compounds may be blended in advance to prepare a mixed solvent to be used.

A liquid medium for forming inclusion crystals may be an inclusion solvent alone or a mixture of an inclusion solvent and a solvent not involved in forming inclusion crystals at a mixable ratio. For example, a single carbonyl-compound solvent or a solvent mixture of two or more carbonyl compounds may be combined with another solvent at a mixable ratio. The additional solvent used may be any mixable solvent, for example, alcohols such as methanol, ethanol and isopropanol; ketones such as acetone, methylethylketone and methylisobutylketone; nitriles such as acetonitrile and propionitrile; ethers such as diethyl ether, diisopropyl ether, dioxane and tetrahydrofuran (THF); aromatic hydrocarbons such as benzene, toluene, cumene, xylenes, mesitylene, diisopropylbenzene and triisopropylbenzene; aliphatic hydrocarbons such as pentane, hexane, cyclohexane and petroleum ethers; halogenated hydrocarbons such as dichloromethane, chloroform, dichloroethane and chlorobutane; pyridines such as pyridine, lutidine and quinoline; tertiary amines such as triethylamine and tributylamine; and polar solvents such as dimethylformamide (DMF), dimethyl imidazolidinone (DMI) and dimethyl sulfoxide (DMSO). A proportion of the additional solvent in the mixture is preferably up to 100 wt %, preferably up to 20 wt %, more preferably up to 10 wt % to the total amount of the carbonyl compound(s).

As used herein, the term "inclusion crystal including a solvent" means that a solvent plays an auxiliary role to form a crystal structure, such that a crystal is formed in a form wherein a solvent is taken up into a crystal lattice thereof, or a complex is formed by a weak interaction between a crystal and a solvent. The inclusion form and the crystal structure are not particularly limited.

The amount of a carbonyl-compound solvent in crystallization or recrystallization is not particularly limited, as far as the amount of the compound of formula [1] in the solvent is below its saturation solubility, but desirably the amount of the solvent is 5 to 150 folds both inclusive by weight, more desirably 8 to 50 folds both inclusive by weight of the amount of the compound of the formula [1].

A temperature for crystallization and recrystallization are not particularly limited, but a temperature within a range from −10° C. to the boiling point of a solvent or a liquid medium is desired. Generally, purification can be performed more sufficiently by a single time of recrystallization, but purification at higher purity can also be realized by performing recrystallization repeatedly. A preferable liquid medium for recrystallization is that consisting of a inclusion solvent alone and it is more preferable to used the same single inclusion solvent in both of crystallization and recrystallization.

A preferable aspect of an inclusion compound obtained by the purification method according to this invention may be the above compound represented by formula [6], where n and m represent an arbitrary integer, preferably an integer selected from the range of 1 to 5.

As stated above, the present invention allows 5'-protected thymidines to be effectively purified.

EXAMPLES

The present invention will be further specifically described in the following examples. The examples are, however, not intended to limit the scope of the invention.

Example 1
Preparation of a Complex of 5'-O-(4,4'-dimethoxytrityl) thymidine-(4-methyl-2-pentanone)(2:1)

To a stirred solution of 40.0 g of thymidine (0.165 mol) in 500 mL of pyridine was added 56.0 g of dimethoxytrityl chloride (0.165 mol), and the mixture was stirred at room temperature for 3 hours. To the mixture, 16.7 g of sodium hydrogen carbonate was added. The resulting mixture was stirred at room temperature for 30 min and evaporated under a reduced pressure. To the residue was added 500 mL of methyl isobutyl ketone (MIBK). To the stirred mixture was added 500 mL of water and the mixture was stirred for 10 min. Then, the organic layer was separated and washed with 500 mL of water. The organic layer was evaporated under a reduced pressure. The residue was recrystallized from 900 mL of methyl isobutyl ketone to give a crystalline product, which was then collected by filtration. The crystalline product was dried in vacuo at 50° C. to a constant weight to give 67.3 g of the product. NMR spectroscopy indicated that the crystalline product included 0.5 molecules of 4-methyl-2-pentanone per one molecule of the desired product. DSC analysis showed a sharp endothermic peak (66.8 J/G) at 137° C., indicating that the product was crystals. TG-DTA analysis showed that crystals including 0.5 molecules of 4-methyl-2-pentanone after drying to its constant weight lost no weight until a temperature at which an endothermic reaction occurred (122 to 132° C.), indicating that the solvent was not attached to the crystals. The product was analyzed by high performance chromatography (HPLC) with a reverse-phase octadecyl silica gel column using a mixture of acetonitrile/water (75/25) as an eluent and using a UV detector (254 nm), indicating a purity of 99.5%. A major impurity was 3',5'-O-bis(4,4'-dimethoxytrityl) thymidine with an HPLC peak area of 0.3%. An yield was 67%.

NMR: δ (CDCl$_3$): 8.7 (s, 1H), 7.6 (s, 1H), 7.2–7.4 (m, 9H), 6.8 (m, 4H), 6.4 (t, 1H), 4.6 (m, 1H), 4.1(m, 1H), 3.8 (s, 6H), 3.4 (m, 2H), 2.3–2.5 (m, 3H including CH$_2$ in MIBK), 2.1 (m, 1.5H: COCH$_3$ in MIBK), 1.7 (m, 0.5H: CH in MIBK), 1.5 (s, 3H), 0.9 (d, 3H: CH$_3$×2 in MIBK) (MIBK: an abbreviation for 4-methyl-2-pentanone); IR: cm$^{-1}$ (KBr): 3163, 1698, 1608, 1509, 1259, 1177, 1098, 1033, 830.

Example 2
Preparation of a Complex of 5'-O-(4,4'-dimethoxytrityl) thymidine-(n-butyl acetate) (2:1)

To a stirred solution of 40.0 g of thymidine (0.165 mol) in 500 mL of pyridine was added 56.0 g of dimethoxytrityl chloride (0.165 mol), and the mixture was stirred at room temperature for 3 hours. To the mixture, 16.7 g of sodium hydrogen carbonate was added. The resulting mixture was stirred at room temperature for 30 min and evaporated under a reduced pressure. To the residue was added 500 mL of n-butyl acetate. To the stirred mixture was added 500 mL of water and the mixture was stirred for 10 min. Then, the organic layer was separated and washed with 500 mL of water. The organic layer was evaporated under a reduced pressure. The residue was recrystallized from 900 mL of n-butyl acetate to give a crystalline product, which was then collected by filtration. The crystalline product was dried in vacuo at 50° C. to a constant weight to give 74.6 g of the product. The product was analyzed by high performance chromatography (HPLC) with a reverse-phase octadecyl silica gel column using a mixture of acetonitrile/water (75/25) as an eluent and using a UV detector (254 nm), indicating a purity of 99.6%. A major impurity was 3',5'-O-bis(4,4'-dimethoxytrityl)thymidine with an HPLC peak area of 0.3%. An yield was 75%.

NMR: δ (CDCl$_3$): 0.9 (t, 1.5H: CH$_3$ in n-butyl acetate), 1.4 (m, 1H: CH$_2$ in n-butyl acetate), 1.5 (s, 3H), 1.6 (m, 1H, CH$_2$ in n-butyl acetate), 2.0 (s, 1.5H: CH$_3$ in n-butyl acetate), 2.3 (m, 1H), 2.4 (m, 1H), 2.6 (m, 1H: OCH$_2$ in n-butyl acetate), 3.3 (dd, 1H), 3.4 (dd, 1H), 3.8 (s, 6H), 4.1 (m, 1H), 4.6 (m, 1H), 6.4 (m, 1H), 6.8 (m, 4H), 7.3 (m, 7H), 7.4 (m, 2H), 7.6 (s, 1H), 8.9 (s, 1H).

Reference Example 1
Production of 3',5'-O-bis(4,4'-dimethoxy trityl)thymidine After the filtrate obtained by the recrystallization in Example 1 was concentrated, the concentrate residue was purified by column chromatography (ethyl acetate/hexane). The purified fraction was concentrated to obtained a powder. The powder thus obtained was then dispersed in diisopropyl alcohol and the precipitate thus formed was recovered by filtration and dried, whereby the titled compound was obtained as a white powder.

$^1$H NMR(400 MHz,CDCl$_3$) δ: 8.1(1H,s), 7.5–7.2(18H, m), 6.8(8H,m), 6.4(1H,m), 4.4(1H,m), 4.1(0.33H,m), 3.8 (1H,m), 3.8(12H,s), 3.2(1H,m), 2.9(1H,m), 1.9(2H,m), 1.4 (3H,m), 1.2(2H,d,J=6 Hz)

Reference Example 2
Production of 5'-O-(tert-butyldimethyl silyl)thymodine

Thymidine (15.0 g) was dissolved in 200 ml of DMF. After 8.16 g of imidazole was dissolved in the resultant solution by addition, 10.8 g of tert-butyldimethylsilyl chloride was then added. DMF (100 ml) was further added and the solution was stirred at room temperature. After 2 hours, extraction using ethyl acetate was carried out and the organic layer was washed by a saturated aqueous solution of sodium chloride and dried with anhydrous magnesium sulfate. After concentration of the extract, the target compound was separated by column chromatography (methanol/chloroform).

The fraction solution including the target compound was prepared and concentrated to obtain 11.3 g of the titled compound (yield; 51%).

$^1$H NMR(400 MHz,CDCl$_3$) δ: 9.2(1H,br), 7.5(1H,s), 6.4 (1H,dd,J=5.6, 8.4 Hz), 4.5(1H,m), 4.1(1H,m), 3.9(1H,dd,J=2.8,11.2 Hz), 3.8(1H,dd,J=2.4,11.2 Hz), 2.9(1H,m), 2.4(1H, m), 2.1(1H,m), 1.9(3H,m), 0.9(9H,s), 0.1(6H,s)

Reference Example 3

Production of 5'-O-(tert-butyldimethylsilyl)-3'-O-(4,4'-dimethoxytrityl)thymidine 5'-O-(tert-butyldimethylsilyl)thymidine (11.3 g) was dissolved in 100 ml of anhydrous pyridine. 4,4'-dimethoxytrityl chloride (11.4 g) was added to the resultant solution and 140 ml of anhydrous pyridine was further added, follow by stirring at 60° C. After the reaction completed, the reaction mixture was neutralized by sodium hydrogen carbonate and pyridine was distilled off. Extraction using ethyl acetate was carried out and the extract was washed by a saturated aqueous solution of sodium chloride and dried with anhydrous magnesium sulfate. The extract was concentrated and purified by column chromatography (ethyl acetate/hexane) to obtain 14.9 g of the titled compound (yield: 71%).

$^1$H NMR(400 MHz,CDCl$_3$) δ: 8.2(1H,s), 7.8(1H,s), 7.5–7.3(9H,m), 6.8(4H,m), 6.4(1H,dd,J=5.6,5.6 Hz), 4.3 (1H,m), 4.1(1H,m), 4.0(1H,m), 3.8(6H,s), 3.7(1H,dd,J=1.6, 11.2 Hz), 3.3(1H,dd,J=8.8,11.2 Hz), 2.0(1.5H,m), 1.9(3H,s), 1.7–1.5(2H,m), 1.3(1.5H,m), 0.8(9H,s), 0.1(3H,s), 0.04(3H, s)

Reference Example 4

Production of 3'-O-(4,4'-dimethoxytrityl)thymidine

5'-O-(tert-butyldimethylsilyl)-3'-O-(4,4'-dimethoxytrityl) thymidine (14.9 g) was dissolved in 200 ml of dry THF. A THF solution (25 ml) of tetrabutylammonium fluoride was added to the resultant solution and 100 ml of dry THF was further added, followed by stirring at room temperature. After 8 hours, concentration and extraction using ethyl acetate was carried out, and the extract was washed by a saturated solution of sodium chloride and dried with anhydrous magnesium sulfate. The extract was then concentrated and purified by column chromatography (ethyl acetate/hexane). The purified preparation was dissolved in chloroform and the solution was dropped into hexane. The precipitate was recovered by filtration and dried to obtain 12.2 g of the titled compound as a white powder (yield: 98%).

$^1$H NMR(400 MHz,CDCl$_3$) δ: 8.7(1H,s), 7.7(1H,s), 7.5–7.2(9H,m), 6.8(4H,m), 6.1(1H,dd,J=5.6,8.8 Hz), 4.0 (1H,m), 3.8(6H,s), 3.7(1H,m), 3.3(1H,m), 2.3(1H,m), 1.9 (1H,m), 1.87(3H,s), 1.7(1H,m)

Comparative Example 1

In respect of an ability to eliminate impurities such as the 3'-substituted isomer [3'-O-(4,4'-dimethoxytrityl)thymidine] or the 3',5'-multisubstituted form [3',5'-O-bis(4,4'-dimethoxytrityl)thymidine], comparison was made between purification methods involving recrystallization from 4-methyl-2-pentanone (MIBK) and involving reprecipitation using dichloromethane as a soluble solvent and hexane as an insoluble solvent. In addition, the results for a recovery of a desired product [5'-O-(4,4'-dimethoxytrityl)thymidine] and for thermal analysis for the crystals obtained (TG-DTA: endothermic peak, DSC: endothermic peak and endothermic energy) were also compared.

TABLE 1

|  | Crude crystals | Purification solvent MIBK | Dichloromethane/hexane |
|---|---|---|---|
| 3'-isomer | 4.0% | 0% | 0.29% |
| Multisubstituted form | 5.0% | 0.24% | 0.61% |
| Yield |  | 91% | 81% |
| DSC Endothermic peak |  | 122/132° C. | 105° C. |
| TG-DTA Endothermic peak |  | 137° C. | 109° C. |
| Endothermic energy |  | 66.8 J/G | 6.2 J/G |

(1) HPLC Conditions for Comparative Example 1 (Analysis of the Amount of the Multisubstituted Form):

Column: Develosil TMS-UG-5, 150 mm×φ4.6;

Flow rate: 1.0 mL/min;

Column temperature: 40° C.;

Detection wavelength: 254 nm;

Mobile phase: gradient conditions (See Table 2).

TABLE 2

| Time (sec) | Liquid B (vol %) |
|---|---|
| 0 | 20 |
| 15 | 70 |
| 35 | 100 |
| 40 | 100 |
| 45 | 20 |
| 60 | stop |

[Liquid A]

100 mL of 100 mM triethylamine-acetic acid (pH 7)/880 mL of water/20 mL of acetonitrile.

[Liquid B]

100 mL of 100 mM triethylamine-acetic acid (pH 7)/900 mL of acetonitrile.

(2) HPLC Conditions in Comparative Example 1 (Analysis of the Amount of the 3'-Isomer):

Column: Develosil TMS-UG-5 150 mm×φ4.6;

Mobile phase: acetonitrile-water (55:45);

Flow rate: 1.0 mL/min;

Column temperature: 40° C.;

Detection wavelength: 254 nm.

(3) Conditions for Thermal Analysis (TG-DTA):

Apparatus: SHIMADZU TG/DTA320 (SII)

Temperature programming rate: 10° C./min

Measurement atmosphere: under nitrogen atmosphere, 200 mL/min.

(4) Conditions for Differential Scanning Calorimetry (DSC):

Apparatus: DSC-7 (Perkin Elmer);

Temperature programming rate: 10° C./min.

According to the present invention, a method capable ass production allows highly pure 5'-protected thymidines e produced more efficiently than conventional methods.

What is claimed is:

1. An inclusion compound represented by formula [5]:

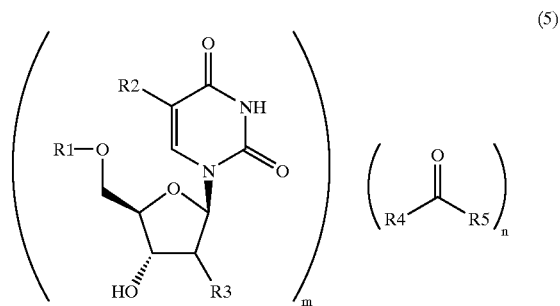

(5)

wherein m and n independently represent an arbitrary integer; $R^1$ represents 4,4'-dimethoxytrityl; $R^2$ represents hydrogen or methyl; $R^3$ represents hydrogen; $R^4$ represents methyl; and $R^5$ represents C2–4 alkyl or C2–4 alkoxy.

2. An inclusion compound represented by formula [6]:

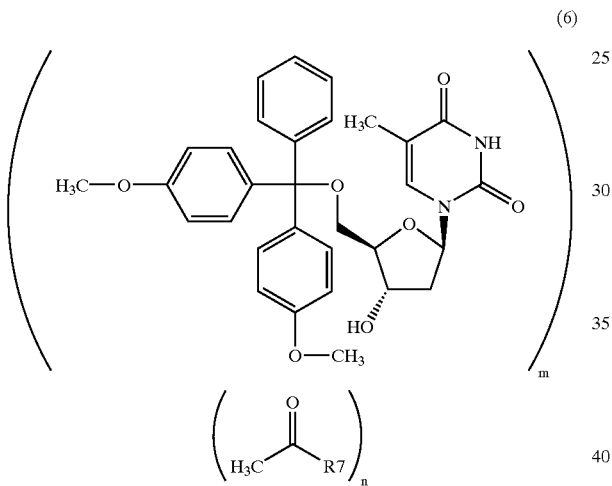

(6)

wherein $R^7$ represents n-butoxy or isobutyl; m and n are arbitrary integers.

3. A method for purifying a 5'-protected thymidine, comprising the steps of:

obtaining a compound represented by formula [1]:

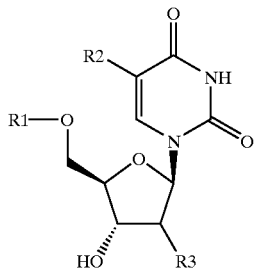

[1]

wherein $R^1$ represents 4,4;-dimethoxytrityl; $R^2$ represents hydrogen or methyl; and $R^3$ represents hydrogen, in the form of inclusion crystals including an inclusion solvent, in a liquid medium comprising the inclusion solvent; and recovering the inclusion crystals from the liquid medium wherein the inclusion solvent is a carbonyl compound represented by formula [2]:

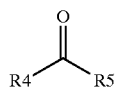

[2]

wherein $R^4$ represents methyl; and $R^5$ represents C2–4 alkyl or C2–4 alkoxy.

4. The purification method as claimed in claim 3 wherein the carbonyl compound is butyl acetate or 4-methyl-2-pentanone.

5. The purification method as claimed in claim 3 wherein a crude preparation comprising the compound of formula [1] and a compound of formula [3]:

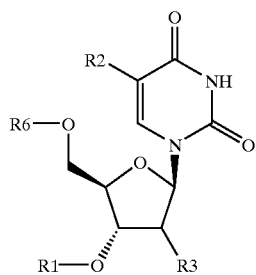

[3]

wherein $R^6$ represents hydrogen or optionally substituted trityl; and $R^1$, $R^2$ and $R^3$ are as defined above, is dissolved in the liquid medium and the compound of formula [3] is removed into the liquid medium by recovering the compound of formula [1] in the form of inclusion crystals from the liquid medium.

6. The purification method as claimed in claim 3 wherein the compound of formula [1] is a compound represented by formula [4]:

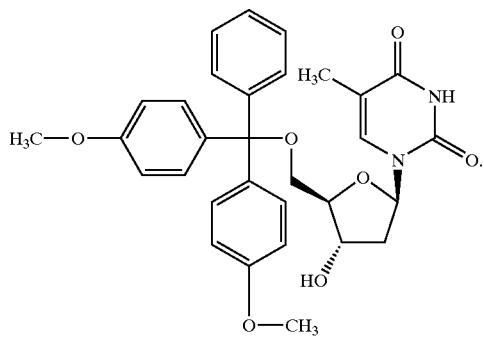

[4]

7. The purification method as claimed in claim 3 wherein the inclusion crystals of the compound of formula [1] including the inclusion solvent are recrystallized from a liquid medium consisting of the inclusion solvent.

8. The purification method as claimed in claim 3 wherein the liquid medium consists of a single inclusion solvent.

* * * * *